(12) United States Patent
Gotou et al.

(10) Patent No.: US 7,413,745 B2
(45) Date of Patent: *Aug. 19, 2008

(54) OIL-BASED COSMETIC PREPARATION

(75) Inventors: Naoki Gotou, Kanagawa (JP); Taro Ehara, Kanagawa (JP); Takahiro Mori, Kanagawa (JP)

(73) Assignee: The Nisshin Oillio Group, Ltd., Chuo-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/264,583

(22) Filed: Nov. 2, 2005

(65) Prior Publication Data

US 2006/0051307 A1    Mar. 9, 2006

Related U.S. Application Data

(63) Continuation of application No. PCT/JP2004/006788, filed on May 13, 2004.

(30) Foreign Application Priority Data

May 13, 2003    (JP) .............................. 2003-135179

(51) Int. Cl.
*A61K 8/02* (2006.01)
(52) U.S. Cl. .................................................. 424/401
(58) Field of Classification Search ................. 424/401
See application file for complete search history.

(56) References Cited

U.S. PATENT DOCUMENTS

| 4,389,346 A * | 6/1983 | Yamada et al. ............... 424/63 |
| 5,436,006 A * | 7/1995 | Hirose et al. ............... 424/401 |
| 6,214,329 B1 * | 4/2001 | Brieva et al. ............... 424/70.7 |
| 2005/0042181 A1 | 2/2005 | Gotou et al. |

FOREIGN PATENT DOCUMENTS

| JP | 51-118843 | 10/1976 |
| JP | 52-048613 | 4/1977 |
| JP | 52-131513 | 11/1977 |
| JP | 53-046890 | 12/1978 |
| JP | 53-46890 B | 12/1978 |
| JP | 54-109917 | 8/1979 |
| JP | 56-032407 | 4/1981 |
| JP | 59-029055 | 7/1984 |
| JP | 1-079106 A | 3/1989 |
| JP | 64-079106 | 3/1989 |
| JP | 5-178734 | 7/1993 |
| JP | 9-235210 | 9/1997 |
| JP | 10-510284 | 10/1998 |
| JP | 10-510284 A | 10/1998 |
| JP | 11-255616 | 9/1999 |
| JP | 11-343223 | 12/1999 |
| JP | 2000-229816 | 8/2000 |
| JP | 2001-158718 | 6/2001 |
| JP | 2001-192559 | 7/2001 |
| JP | 2002-154916 | 5/2002 |
| JP | 2003-063927 | 3/2003 |
| WO | 03/082453 A1 | 10/2003 |

OTHER PUBLICATIONS

International Search Report dated Aug. 31, 2004.
Please note that a copy of the International Search Report where documents JP 1-079106 and JP 10-510284 cited above was filed on Nov. 2, 2005.

\* cited by examiner

*Primary Examiner*—Johann R. Richter
*Assistant Examiner*—Konata M George
(74) *Attorney, Agent, or Firm*—Buchanan Ingersoll & Rooney PC

(57) ABSTRACT

An oil-based cosmetic preparation contains (a) an oily gelling agent, (b) an oil-based ingredient, and (c) at least one selected from the group consisting of ester compounds represented by formula (I) which are reaction products of ditrimethylolpropane with fatty acid, polycondensates of ditrimethylolpropane with polycarboxylic acid, polycondensates of the ester compound of formula (I) with polycarboxylic acid, polycondensates of fatty acid with the polycondensate of ditrimethylolpropane with polycarboxylic acid, and polycondensates of ditrimethylolpropane, fatty acid and polycarboxylic acid, with the component (c) having a hydroxyl value (OHV) in the range of 10 to 150. The oil-based cosmetic preparation has excellent feeling realized by the use, provides a make-up coverage with satisfactory luster and moisturizing feel, and exhibits excellent shape retention properties.

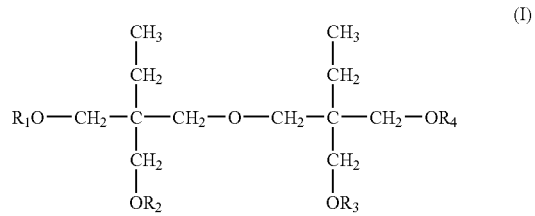

10 Claims, No Drawings

OIL-BASED COSMETIC PREPARATION

BACKGROUND OF THE INVENTION

The present invention relates to an oil-based cosmetic preparation, and more particularly to an oil-based cosmetic preparation with feeling realized by the use of it and satisfactory shape retention properties, capable of providing an excellent make-up coverage with luster and moisturizing feel.

Conventionally, consideration has been given to selection of the ingredients such as an oily gelling agent, solid oil, semi-solid oil, liquid oil and the like, and alternation of the contents of those ingredients in the preparation of oil-based cosmetics in order to obtain various sensory satisfactions and make-up effects. In the solid type oil-based cosmetic products, such as lipstick and stick foundation, the feeling realized by the use of them, long-lasting make-up, luster of the coverage, and the like are controlled by blending solid oil components including ceresin wax, candelilla wax and the like, with the shape retention properties being taken into consideration. In the paste type oil-based cosmetic products such as liquid rouge, liquid eye-shadow and the like, the feeling realized by the use of them, long-lasting make-up results, luster of the coverage and the like are controlled by using a gelling agent including dextrin fatty acid esters, silicic acid anhydride and the like.

With respect to the lipstick, the combination of a polyethylene wax and a liquid oil component having in its structure one hydroxyl group is employed to effectively revive the color (for example, see Japanese Patent Unexamined Publication (JP Kokai) 2001-158718). However, the glycerin fatty acid esters and the like given as examples cannot sufficiently meet the requirements of the shape retention properties and the feeling realized by the use at the same time. When the shape retention properties are improved, the feeling realized by the use may be impaired; while the improvement of the feeling realized by the use may degrade the shape retention properties.

In the solid cosmetic products, there is known the technique that a dextrin fatty acid ester, a liquid oil component having a hydroxyl value of 20 or less, and a particular silica are blended into the cosmetic formulation for the purpose of improving the feeling realized by the use while ensuring a sheer transparent coverage (see, for example, JP Kokai No. Hei 11-255616). However, since the silica is contained as the essential ingredient, a sufficient degree of luster cannot always be obtained if desired, although non-sticky feeling to the skin and excellent preservation stability can be ensured.

Further, a dextrin fatty acid ester and heavy liquid isoparaffin are blended into the cosmetic formulation to obtain a high degree of luster (see, for example, JP Kokai No. Hei 9-235210 and No. 2000-229816). However, the obtained cosmetics cannot easily spread and may become sticky when applied to the skin due to the presence of the heavy liquid paraffin, although sufficient luster can be obtained.

Furthermore, polyol condensate esters, neopentyl alcohol esters or the like, each having the characteristics similar to those of the skin surface lipids of human are known as oil-based vehicles (see, for example, Japanese Patent Examined Publication (JP Kokoku) No. Sho 53-46890 and No. Sho 59-29055). Those oil-based vehicles are of a full-ester type without hydroxyl group, so that there are the problems that the oil-based vehicles cannot set efficiently by use of the gelling agent, and the poor hydrous tendency cannot offer sufficient moisturizing feel.

DISCLOSURE OF INVENTION

In light of the above, there is an increasing demand for development of an oil-based cosmetic preparation which can smoothly spread when applied to the skin so as to ensure the feeling realized by the use of it, and at the same time, which can provide a make-up coverage with luster and moisturizing feel, and exhibit satisfactory shape retention properties.

Under such current circumstances, the inventors of the present invention have studied intensively to solve the above-mentioned problems. As a result of the study, it has been found that a formulation containing an oily gelling agent, an oil-based ingredient and a ditrimethylolpropane derivative can produce an oil-based cosmetic preparation that can smoothly spread when applied to the skin, offer long-lasting make-up results, provide a make-up coverage with luster and moisturizing feel, and exhibit good shape retention properties. The present invention has been thus accomplished.

Namely, the present invention provides an oil-based cosmetic preparation comprising:

(a) an oily gelling agent;

(b) an oil-based ingredient; and (c) at least one selected from the group consisting of ester compounds represented by the following formula (I) which are reaction products of ditrimethylolpropane with fatty acids, polycondensates of ditrimethylolpropane with polycarboxylic acid, polycondensates of the ester compound of the following formula (I) with polycarboxylic acid, polycondensates of fatty acid with the polycondensate of ditrimethylolpropane with polycarboxylic acid, and polycondensates of ditrimethylolpropane, fatty acid and polycarboxylic acid,

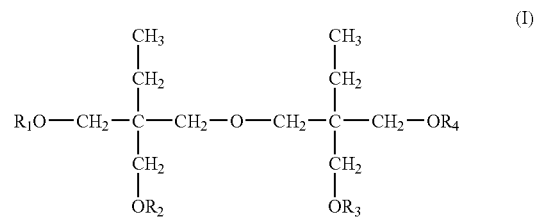

wherein $R_1$ to $R_4$ are each independently a hydrogen atom or a fatty acid residue, provided that at least one of $R_1$ to $R_4$ represents a fatty acid residue, with the component (c) having a hydroxyl value (OHV) ranging from 10 to 150.

The above-mentioned polycondensates of fatty acid with the polycondensate of ditrimethylolpropane with polycarboxylic acid indicate polycondensates obtainable by subjecting a polycondensate of ditrimethylolpropane with a polycarboxylic acid and a fatty acid to an esterification reaction.

The present invention provides an oil-based cosmetic preparation comprising the components (a), (b) and (c), wherein the component (a) comprises at least one oily gelling agent selected from the group consisting of paraffin wax, ceresin wax, microcrystalline wax, Fischer-Tropsch wax, polyethylene wax, carnauba wax, and candelilla wax.

Also, the present invention provides an oil-based cosmetic preparation comprising the components (a), (b) and (c), wherein the component (a) comprises at least one oily gelling agent selected from the group consisting of 12-hydroxystearic acid, dextrin fatty acid esters, sucrose fatty acid esters, metallic soaps, silica, glyceryl (behenate/eicosanedioate), and organic modified clay minerals.

BEST MODE FOR CARRYING OUT THE INVENTION

Any gelling agents generally used in the cosmetics to solidify or gelatinize the oil-based ingredients can be adopted as the component (a) for use in the present invention without any particular limitations. For the solid type cosmetic products such as lipstick and stick foundation, preferably used are oily gelling agents that assume a solid state at ambient temperature. In particular, it is preferable to use at least one gelling agent selected from the group consisting of paraffin wax, ceresin wax, microcrystalline wax, Fischer-Tropsch wax, polyethylene wax, carnauba wax, and candelilla wax. This is because the above-mentioned waxes can sufficiently exhibit a solidifying function inherent in the respective waxes when blended into the preparation of the present invention, so that even a small amount can offer satisfactory shape retention properties. The commercially available products of the above-mentioned waxes include Purified carnauba wax No. 1 (Cerarica Noda Co., Ltd.), Ozokerite wax SP-273P (Strahl & Pitsh Inc.), Microwax 190Y (Exxon Mobil Corp.), Himic 1080/2095 (Nippon Seiro Co., Ltd.), Sanwax E-200, E-300 (Sanyo Chemical Industries, Ltd.), Mobil 180 (Exxon Mobil Corp.), Starwax 100 (Bareco Products), Nisseki Microwax 180 (Nippon Oil Company, Limited), Fischer-Tropsch wax FT-95, FT100H, FT-150, FT-200 (Sasol Wax Limited), BeSquare 180, 185, 190, 195 (Bareco Products), Polywax 500, 655 (Bareco Products), Sasol Wax H1, C1, C2 (Sasol Wax Limited), and the like.

For the paste type cosmetic products such as liquid rouge and liquid eye-shadow, it is preferable to use at least one oily gelling agent selected from the group consisting of 12-hydroxystearic acid, dextrin fatty acid esters, sucrose fatty acid esters, metallic soaps, silica, glyceryl (behenate/eicosanedioate), and organic modified clay minerals. The above-mentioned glyceryl (behenate/eicosanedioate) is an oligomer ester of glycerol with behenic acid and eicosanedioic acid, for example, including as a commercially available product, "Nomcort HK-G" (The Nisshin Oillio Group, Ltd.).

By using those gelling agents, the oil-based cosmetic preparations can be provided with feeling realized by the use of them and can offer a make-up coverage with excellent luster. This is because the above-mentioned gelling agents can sufficiently exhibit their gelling function and a satisfactory gel state can be attained even by a small amount.

In the above, 12-hydroxystearic acid is a fatty acid having hydroxyl group, which can be produced, for example, by hydrogenating ricinoleic acid obtainable from castor oil. The dextrin fatty acid ester is an ester compound of oil-soluble straight-chain or branched saturated or unsaturated fatty acid having 8 to 24 carbon atoms (preferably 14 to 18 carbon atoms) and dextrin having an average polymerization degree of 10 to 50 (preferably 20 to 30). To be more specific, there can be employed dextrin palmitate, dextrin palmitate/2-ethylhexanoate, dextrin stearate, dextrin palmitate/stearate, dextrin oleate, dextrin isopalmitate, dextrin isostearate and the like. Those dextrin fatty acid esters may be used alone or in combination. There can be given as examples of the commercially available dextrin palmitate products, e.g., "Rheopearl KL" and "Rheopearl TL" (made by Chiba Seifun Co., Ltd.); and the commercially available dextrin palmitate/2-ethylhexanoate product, e.g., "Rheopearl TT" (made by Chiba Seifun Co., Ltd.).

With respect to the sucrose fatty acid esters, any sucrose fatty acid esters typically used in the cosmetics can be used. In particular, fatty acid esters prepared from palmitic acid, stearic acid, behenic acid, oleic acid, lauric acid and the like are preferable.

The metallic soaps include aluminum isostearate, aluminum stearate, calcium stearate and the like. The organic modified clay minerals include water-swelling clay minerals treated with quaternary ammonium salts. For example, organic modified bentonite products "Benton 38" and "Benton 27" (both are made by NL Industry Inc.) can be given as examples of the commercially available products.

With respect to the above-mentioned silica, any silica products generally used for the cosmetics, for example, fumed, porous, non-porous, and spherical silica products are usable. In particular, fumed silica is preferable. The fumed silica, which can be obtained, for example, by subjecting silicon tetrachloride to hydrolysis in the presence of hydrogen and oxygen flame, includes the commercially available products such as "Aerosil 50", "Aerosil 130", "Aerosil 200", "Aerosil 200V", "Aerosil 200CF", "Aerosil 200FAD", "Aerosil 300", "Aerosil 300CF" and "Aerosil 380", made by Nippon Aerosil Co., Ltd. Those silica products can be used alone or in combination. In addition, the fumed silica may preferably have a primary particle diameter of 50 nm or less, more preferably 20 nm or less.

Hydrophobic fumed silica may be used, which is obtainable by subjecting the above-mentioned fumed silica to hydrophobic treatment. To make the fumed silica hydrophobic, the fumed silica may be trimethylsiloxy-treated using trimethylchlorosilane and hexamethyldisilazane, surface-modified with octylsilane, coated with a film of methylhydrogen polysiloxane by curing, coated with metallic soap, and the like. Examples of the commercially available hydrophobic fumed silica products are "Aerosil R-972", "Aerosil R-972V", "Aerosil R-972CF", "Aerosil R-974", "Aerosil R-976S", "Aerosil RX200", "Aerosil RY200", "Aerosil R-202", "Aerosil R-805", "Aerosil R-812", "Aerosil RX200" and "Aerosil RA200H", made by Nippon Aerosil Co., Ltd.; "Taranox 500" (made by Tarco Co., Ltd.); and "Cabosil TS-530" (made by Cabot Corp.).

In any case, one kind of oily gelling agent as the component (a) may be used alone or two or more gelling agents may be used in combination if necessary.

The amount of the component (a) in the oil-based cosmetic preparation of the present invention, which is varied depending upon the ingredients to be chosen, desired quality, shape or form of the cosmetic product, and the like, may preferably be 0.5 to 30% by mass, more preferably 1 to 20% by mass, with respect to the total mass of the oil-based cosmetic preparation. When the amount of component (a) is within the above-mentioned range, excellent shape retention properties and feeling realized by the use can be obtained, and at the same time, the cosmetic preparation can provide a long-lasting make-up coverage having sufficient luster.

With respect to the component (b) for use in the present invention, any oil-based ingredients typically used for the cosmetics can be used with no limitation. Regardless of origin of oil, i.e., whether the oil-based ingredient is from animal oils, vegetable oils, synthetic oils or the like, and regardless of properties of oil, i.e., whether the oil-based ingredient is a semi-solid oil, liquid oil, volatile oil or the like, any hydrocarbons, fats and oils, waxes, hardened oils, ester oils, fatty acids, higher alcohols, silicone oils, fluorinated oils, lanolin derivatives and the like can be employed. Specific examples include the hydrocarbons such as liquid paraffin, heavy liquid isoparaffin, alpha-olefin oligomer, squalane, vaseline, polyisobutylene, polybutene, montan wax and the like; fats and oils such as olive oil, castor oil, jojoba oil, mink oil, macadamia nut oil and the like; waxes such as bees wax, candelilla wax, spermaceti wax and the like; eaters such as Japan wax, cetyl isooctanoate, isopropyl myristate, isopropyl palmitate, octyldodecyl myristate, polyglyceryl diisostearate, polyglyceryl triisostearate, diglyceryl triisostearate, polyglyceryl tetraisostearate, diglyceryl tetraisostearate, glyceryl trioctanoate, diisostearyl malate, neopentyl glycol dioctanoate, propylene glycol dicaprate, cholesterol fatty acid esters and the like; fatty acids such as stearic acid, lauric acid, myristic acid, behenic acid, isostearic acid, oleic acid and the like; higher alcohols such as stearyl alcohol, cetyl alcohol, lauryl alcohol, oleyl alcohol, isostearyl alcohol, behenyl alcohol, and the like; silicones such as dimethyl polysiloxane with a low degree of polymerization, dimethyl polysiloxane with a high degree of polymerization, methylphenyl polysiloxane, decamethylcyclopentasiloxane, octamethylcyclotetrasiloxane, polyether-modified polysiloxanes, polyoxyalkylene-alkylmethyl polysiloxane-methyl polysiloxane copolymers, alkoxy-modified polysiloxanes and the like; fluorinated oils such as perfluorodecane, perfluorooctane, perfluoropolyether and the like; and lanolin and derivatives thereof such as liquid lanolin, lanolin acetate, liquid lanolin acetate, isopropyl esters of lanolin fatty acid, lanolin alcohols and the like. The component (b) for use in the present invention is defined as to exclude the component (c) to be explained later.

The content of the component (b) in the oil-based cosmetic preparation of the present invention is not particularly limited, but may preferably be 1 to 95% by mass, more preferably 3 to 70% by mass, with respect to the total mass of the oil-based cosmetic preparation. When the content of component (b) is within the above-mentioned range, excellent shape retention properties and feeling realized by the use can be obtained, and at the same time, the resultant cosmetic preparation can provide a long-lasting make-up coverage with sufficient luster.

The ratio by mass of the component (a) to the component (b), that is, the (a)/(b) ratio may be in the range of 1/199 to 9/1, more preferably 1/99 to 4/1. When the (a)/(b) ratio is within the above-mentioned range, it is possible to obtain excellent shape retention properties and feeling realized by the use of the resultant product, and at the same time, to ensure the long-lasting make-up results.

The component (c) for use in the oil-based cosmetic preparation the present invention includes at least one selected from the group consisting of ester compounds represented by the following formula (I) which are reaction products of ditrimethylolpropane with fatty acid, polycondensates of ditrimethylolpropane with polycarboxylic acid, polycondensates of the ester compound of formula (I) with polycarboxylic acid, polycondensates of fatty acid with the polycondensate of ditrimethylolpropane with polycarboxylic acid, and polycondensates of ditrimethylolpropane, fatty acid and polycarboxylic acid,

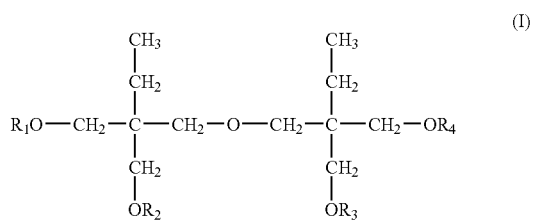

wherein $R_1$ to $R_4$ are each independently hydrogen atom or a fatty acid residue, provided that at least one of $R_1$ to $R_4$ represents a fatty acid residue.

The fatty acid for constituting the component (c) may preferably be a straight-chain or branched fatty acid having 5 to 28 carbon atoms. More preferably used are branched fatty acids. Examples of those branched fatty acids are pivalic acid, isoheptanoic acid, 4-ethylpentanoic acid, isooctylic acid, 2-ethylhexanoic acid, 4,5-dimethylhexanoic acid, 4-propylpentanoic acid, isononanoic acid, 2-ethylheptanoic acid, 3,5,5-trimethylhexanoic acid, isodecanoic acid, isododecanoic acid, 2-methyldecanoic acid, 3-methyldecanoic acid, 4-methyldecanoic acid, 5-methyldecanoic acid, 6-methyldecanoic acid, 7-methyldecanoic acid, 9-methyldecanoic acid, 6-ethylnonanoic acid, 5-propyloctanoic acid, isolauric acid, 3-methylhendecanoic acid, 6-propylnonanoic acid, isotridecanoic acid, 2-methyldodecanoic acid, 3-methyldodecanoic acid, 4-methyldodecanoic acid, 5-methyldodecanoic acid, 11-methyldodecanoic acid, 7-propyldecanoic acid, isomyristic acid, 2-methyltridecanoic acid, 12-methyltridecanoic acid, isopalmitic acid, 2-hexyldecanoic acid, 14-methylpentadecanoic acid, 2-ethyltetradecanoic acid, isostearic acid, methyl-branched isostearic acid, 2-heptylundecanoic acid, 2-isoheptylisoundecanoic acid, 2-ethylhexadecanoic acid, 14-ethylhexadecanoic acid, 14-methylheptadecanoic acid, 15-methylheptadecanoic acid, 16-methylheptadecanoic acid, 2-butyltetradecanoic acid, isoarachic acid, 3-methylnonadecanoic acid, 2-ethyloctadecanoic acid, isohexacosanoic acid, 24-methylheptacosanoic acid, 2-ethyltetracosanoic acid, 2-butyldocosanoic acid, 2-hexylicosanoic acid, 2-octyloctadecanoic acid and 2-decylhexadecanoic acid. Those fatty acids can be used alone or in combination. Among those fatty acids, preferred are fatty acids having 8 to 18 carbon atoms, in particular, branched saturated fatty acids having 8 to 18 carbon atoms, such as isooctylic acid (preferably 2-ethylhexanoic acid, 4,5-dimethylhexanoic acid), isononanoic acid (preferably 2-ethylheptanoic acid, 3,5,5-trimethylhexanoic acid), isopalmitic acid, isotridecanoic acid, isostearic acid (preferably methyl-branched isostearic acid, 2-heptylundecanoic acid, 2-isoheptylisoundecanoic acid), and the like.

With respect to the straight-chain fatty acids, there can be employed straight-chain fatty acids having 6 to 28 carbon atoms, for example, straight-chain saturated acids such as caproic acid, caprylic acid, octylic acid, nonylic acid, decanoic acid, dodecanoic acid, lauric acid, tridecanoic acid, myristic acid, palmitic acid, stearic acid, behenic acid and the like; and straight-chain unsaturated fatty acids such as caproleic acid, undecylenic acid, myristoleic acid, palmitoleic acid, oleic acid, elaidic acid, gondoic acid, erucic acid, brassic acid and the like. Those fatty acids can be used alone or in combination.

The ester compound as the component (c) in the present invention includes at least one ester compound selected from mono-, di-, tri- and tetra-ester compounds.

The polycarboxylic acids used to prepare the polycondensates, serving as the component (c) in the present invention, preferably include dibasic carboxylic acids having 2 to 10 carbon atoms such as succinic acid, adipic acid, azelaic acid, sebacic acid and the like. Those polycarboxylic acids can be used alone or in combination.

The component (c) preferably has a hydroxyl value (OHV) (hereinafter referred to as "OHV" simply) ranging from 10 to 150, more preferably 30 to 150, and most preferably 40 to 100. When the OHV is within the above-mentioned range, the compatibility of the component (c) with other oil ingredients becomes better, and at the same time, the hydration properties are improved to easily obtain the moisturizing feeling. The term OHV herein used is a value determined by the hydroxyl value measurement test method in accordance with the Japanese Standards of Cosmetic Ingredients. Preferably, the component (c) for use in the present invention may assume a liquid state at room temperature, having a viscosity of 100 to 30,000 mPa.s at 25° C.

The component (c) for use in the present invention can be prepared, for example, by adding 1.5 to 3.5 equivalents of a fatty acid and/or polycarboxylic acid to one equivalent of ditrimethylolpropane, and carrying out a reaction of esterification and/or dehydration condensation at 180 to 240° C. in the absence or presence of a catalyst (e.g., tin chloride). After completion of the reaction, the catalyst is removed from the reaction mixture by adsorption treatment or the like, and low-molecular weight components such as an unreacted raw material are eliminated by distillation or the like, thereby obtaining the final product.

The content of the component (c) is not particularly limited, and may be determined with the feeling realized by the use, molding properties, shape retention properties and the like being taken into consideration. Preferably, the content of the component (c) may be in the range of 1 to 90% by mass, more preferably 5 to 70% by mass, and further preferably 5 to 50% by mass, with respect to the total mass of the oil-based cosmetic preparation. When the content is within the above-mentioned range, satisfactory products can be obtained in terms of the feeling realized by the use, the luster of the make-up coverage and moisturizing feel.

In the present invention, the component (c) may preferably include 20% by mass or more of the ester compound represented by formula (I) or the polycondensate of ditrimethylolpropane, fatty acid and polycarboxylic acid, or a mixture of the ester compound and the polycondensate. The content of the above-mentioned ester compound or polycondensate or a mixture thereof in the component (c) may preferably be 90% by mass or less, more preferably 70% by mass or less.

In addition to the above-mentioned essential ingredients, various additional components can be incorporated into the formulation for the oil-based cosmetic preparation of the present invention if necessary so far as the effects of the present invention will not be damaged. For example, a powder material, surfactant, UV light absorber, moisturizing agent, water-base component, film-forming agent, anti-browning agent, antioxidant, anti-foamer, essence, preservative, perfume and the like may be added appropriately to fulfill the respective effects.

Among the above components, the powder material is added for the purpose of improving feeling realized by the use and adjusting the color tone. Inorganic powders, optical powders, organic powders, pigment powders, metallic powders, composite powders and the like can be used regardless of the shape, that is, spheres, plates, needles or the like, regardless of the particle diameter, that is, aerosol particles, fine particles, pigment-grade particles or the like, and regardless of the particle structure, that is, porous, non-porous or the like. Specific examples of the powder materials are inorganic white pigments such as titanium oxide, zinc oxide, cerium oxide, barium sulfate and the like; inorganic colored pigments such as iron oxide, carbon black, chromium oxide, chromium hydroxide, iron blue, ultramarine and the like; white extender pigments such as talc, muscovite, phlogopite, lepidolite, biotite, synthetic mica, sericite, synthetic sericite, kaolin, silicon carbide, bentonite, smectite, aluminum oxide, magnesium oxide, zirconium oxide, antimony oxide, diatomite, aluminum silicate, aluminum magnesium metasilicate, calcium silicate, barium silicate, magnesium silicate, calcium carbonate, magnesium carbonate, hydroxyapatite, boron nitride and the like; optical powders such as titanium dioxide-coated mica, titanium dioxide-coated bismuth oxychloride, iron oxide-coated titanated mica, iron blue-coated titanated mica, carmine-treated titanated mica, bismuth oxychloride, fish scale flakes, laminated powder of epoxy resin coated polyethylene terephthalate-aluminum, laminated powder of polyethylene terephthalate-polyolefin and the like; organic high-molecular weight resin powders such as polyamide resin, polyethylene resin, polyacrylic resin, polyester resin, fluoroplastic, cellulose resin, polystyrene resin, copolymer resin including styrene-acryl copolymer resin, polypropylene resin, silicone resin, urethane resin and the like; organic low-molecular weight powders such as zinc stearate, N-acyl-lysine and the like; organic natural powders such as starch, silk powder, cellulose powder and the like; organic pigment powders such as Red No. 201, Red No. 202, Red No. 205, Red No. 226, Red No. 228, Orange No. 203, Orange No. 204, Blue No. 404, Yellow No. 401 and the like; organic pigment powders containing zirconium, barium or aluminum lake such as Red No. 3, Red No. 104, Red No. 106, Orange No. 205, Yellow No. 4, Yellow No. 5, Green No. 3, Blue No. 1 and the like; metallic powders such as aluminum powder, gold powder, silver powder and the like; and composite powders such as titanium oxide fine particles-coated titanated mica, zinc oxide fine particles-coated titanated mica, barium sulfate-coated titanated mica, titanium oxide-containing silicon dioxide, zinc oxide-containing silicon dioxide and the like. Those powder materials may be used alone or in combination, and another composite powders made from the above powders can also be used. The above-mentioned powders may be surface-treated with at least one material selected from fluorine-containing compounds, silicone compounds, metallic soaps, lecithin, hydrogenated lecithin, collagen, hydrocarbons, higher fatty acids, higher alcohols, esters, waxes, surfactants and the like.

The surfactants, for example, nonionic surfactants, anionic surfactants, cationic surfactants and amphoteric surfactants can be used with no particular limitation if they are conventionally used for the cosmetics. Further, the UV absorber includes, for example, benzophenone compounds, PABA compounds, cinnamates, salicylates, 4-tert-butyl-4'-methoxydibenzoylmethane, oxybenzone and the like; and the moisturizing agent includes, for example, protein, mucopolysaccharide, collagen, elastin, keratin and the like.

The water-base ingredients may be water and any water-soluble substances. In addition to water, glycols such as propylene glycol, 1,3-butylene glycol, dipropylene glycol, polyethylene glycol and the like, glycerols such as glycerin, diglycerin, polyglycerin and the like, and plant extracts of aloe, witch hazel, hamamelis, cucumber, lemon, lavender, rose and the like can be given as examples.

The antioxidant includes, for example, tocopherols, ascorbic acid and the like. The essence includes, for example, vitamins, anti-inflammatory agents, crude drugs and the like; and the preservative includes, for example, p-hydroxybenzoate esters, phenoxyethanols and the like.

According to the application, the oil-based cosmetic preparation of the present invention may be in any state, for example, a solid (e.g., in the form of a stick or plate), paste, liquid or the like, and finished into any product form, for example, lipstick, lip gloss, lip cream, foundation, cheek rouge, eye-shadow, eyeliner, mascara, sunscreen lotion, cleansing oil and the like. There is no particular limitation on the manufacturing process of those cosmetic products, which can be prepared by any conventional methods.

The present invention will now be explained in detail by referring to the following examples, which are not intended to be limiting of the present invention.

PREPARATION EXAMPLE 1

Preparation of polycondensate of ditrimethylolpropane, isostearic acid and sebacic acid A four-necked flask (1 L) equipped with a stirrer, a thermometer, a nitrogen gas inlet, and a water separator was charged with 168 g (0.8 mol) of ditrimethylolpropane (ditrimethylolpropane made by Koei Chemical Co., Ltd.), 392 g (1.3 mol) of isostearic acid ("Prisorine 3505" made by Uniquema), and 41 g (0.2 mol) of sebacic acid (sebacic acid made by Kokura Synthetic Industries, Ltd.). Xylol was also added as a solvent for reflux in an amount of 5% by mass of the total mass of the charged materials. The mixture was allowed to react at 180 to 240° C. for 6 hours with stirring. After completion of the reaction, the mixture was decolorized with activated clay and deodorized by the conventional method, so that 436 g of a polycondensate of ditrimethylolpropane, isostearic acid and sebacic acid was obtained. The OHV of the polycondensate was 92.

PREPARATION EXAMPLE 2

Preparation of ester compound of ditrimethylolpropane and 2-ethylhexanoic acid

A four-necked flask (1 L) equipped with a stirrer, a thermometer, a nitrogen gas inlet, and a water separator was charged with 211 g (0.8 mol) of ditrimethylolpropane (ditrimethylolpropane made by Koei Chemical Co., Ltd.) and 389 g (2.7 mol) of 2-ethylhexanoic acid (octylic acid made by Chisso Corporation). Xylol was also added as a solvent for reflux in an amount of 5% by mass of the total mass of the charged materials. The mixture was allowed to react at 180 to 240° C. for 19 hours with stirring. After completion of the reaction, the mixture was decolorized with activated clay and deodorized by the conventional method, so that 421 g of an ester compound of ditrimethylolpropane and 2-ethylhexanoic acid was obtained. The OHV of the ester compound was 89.

COMPARATIVE PREPARATION EXAMPLE 1

Preparation of tetra-ester compound of ditrimethylolpropane and 2-ethylhexanoic acid A four-necked flask (1 L) equipped with a stirrer, a thermometer, a nitrogen gas inlet, and a water separator was charged with 185 g (0.7 mol) of ditrimethylolpropane (ditrimethylolpropane made by Koei Chemical Co., Ltd.) and 415 g (2.9 mol) of 2-ethylhexanoic acid (octylic acid made by Chisso Corporation). Xylol was also added as a solvent for reflux in an amount of 5% by mass of the total mass of the charged materials. The mixture was allowed to react at 180 to 240° C. for 30 hours with stirring. After completion of the reaction, the mixture was decolorized with activated clay and deodorized by the conventional method, so that 390 g of a tetra-ester compound of ditrimethylolpropane and 2-ethylhexanoic acid (as represented by the following formula II) was obtained. The OHV of the tetra-ester compound was 1.

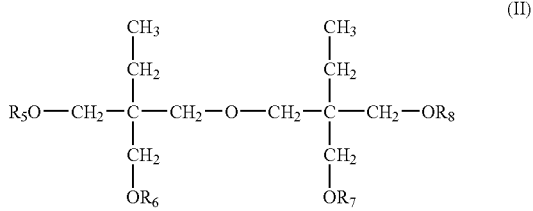

wherein $R_5$ to $R_8$ are each a 2-ethylhexanoic acid residue.

EXAMPLES 1 TO 7 AND COMPARATIVE EXAMPLES 1 TO 5

Lipstick

Production of Lipsticks

Lipsticks with the formulations as shown in Table 1 were produced. Each of the produced lipsticks was evaluated by a sensory test in terms of the feeling realized by the use, luster of the coverage, and moisturizing feel. In addition, each lipstick was placed under high temperatures to evaluate the shape retention properties.

TABLE 1

| | | Examples (unit: % by mass) | | | | | | |
|---|---|---|---|---|---|---|---|---|
| No. | Ingredients | 1 | 2 | 3 | 4 | 5 | 6 | 7 |
| 1 | Ceresin wax | 3 | 3 | 3 | 10 | 3 | 3 | — |
| 2 | Candelilla wax | 3 | 3 | 3 | 10 | 3 | 3 | — |
| 3 | Microcrystalline wax | 6 | 6 | 6 | 10 | 6 | 6 | 8 |
| 4 | Polyethylene wax | 6 | 6 | 6 | — | 6 | 6 | 8 |
| 5 | Dextrin palmitate | — | — | — | — | — | — | — |
| 6 | Diglyceryl triisostearate | 10 | 10 | — | 10 | — | 20 | 10 |
| 7 | Propylene glycol dicaprate | 34.3 | 14.3 | 2.3 | 12.3 | 4.3 | 9.3 | 16.3 |
| 8 | Heavy liquid isoparaffin | 5 | 5 | 1 | 5 | — | 20 | 5 |
| 9 | Liquid lanolin acetate | 5 | 5 | 1 | 5 | — | 20 | 5 |
| 10 | Ester compound of Prep. Ex. 2 | 20 | 20 | — | 15 | 70 | — | 20 |
| 11 | Polycondensate of Prep. Ex. 1 | — | 20 | 70 | 15 | — | 5 | 20 |
| 12 | Tetra-ester compound of Comp. Prep. Ex. 1 | — | — | — | — | — | — | — |
| 13 | Dimethyldichlorosilane-treated fumed silica [(1)] | — | — | — | — | — | — | — |
| 14 | Silica beads [(2)] | — | — | — | — | — | — | — |
| 15 | Fluorinated red oxide-coated mica [(3)] | 2 | 2 | 2 | 2 | 2 | 2 | 2 |
| 16 | Silicone-treated titanated mica [(4)] | 2 | 2 | 2 | 2 | 2 | 2 | 2 |
| 17 | Red No. 202 | 0.1 | 0.1 | 0.1 | 0.1 | 0.1 | 0.1 | 0.1 |

TABLE 1-continued

| No. | Ingredients | | | | | | | |
|---|---|---|---|---|---|---|---|---|
| 18 | Yellow No. 4 | 0.6 | 0.6 | 0.6 | 0.6 | 0.6 | 0.6 | 0.6 |
| 19 | Titanium oxide | 1.5 | 1.5 | 1.5 | 1.5 | 1.5 | 1.5 | 1.5 |
| 20 | Black iron oxide | 0.1 | 0.1 | 0.1 | 0.1 | 0.1 | 0.1 | 0.1 |
| 21 | 2-ethylhexyl p-methoxycinnamate | 1 | 1 | 1 | 1 | 1 | 1 | 1 |
| 22 | Propyl p-hydroxybenzoate | 0.1 | 0.1 | 0.1 | 0.1 | 0.1 | 0.1 | 0.1 |
| 23 | 2,6-di-tert-butyl-p-cresol | 0.1 | 0.1 | 0.1 | 0.1 | 0.1 | 0.1 | 0.1 |
| 24 | dl-alpha-tocopherol | 0.1 | 0.1 | 0.1 | 0.1 | 0.1 | 0.1 | 0.1 |
| 25 | Perfume | 0.1 | 0.1 | 0.1 | 0.1 | 0.1 | 0.1 | 0.1 |
| Total | | 100 | 100 | 100 | 100 | 100 | 100 | 100 |

Evaluation items & results

| | | | | | | | | |
|---|---|---|---|---|---|---|---|---|
| (1) | Ease of use | ◎ | ◎ | ◎ | ○ | ◎ | ◎ | ◎ |
| (2) | Luster | ◎ | ◎ | ◎ | ○ | ◎ | ◎ | ◎ |
| (3) | Moisturizing feel | ◎ | ◎ | ◎ | ◎ | ◎ | ○ | ◎ |
| (4) | Shape retention properties | ◎ | ◎ | ◎ | ◎ | ◎ | ○ | ◎ |

| | | Comparative Examples | | | | |
|---|---|---|---|---|---|---|
| No. | Ingredients | 1 | 2 | 3 | 4 | 5 |
| 1 | Ceresin wax | 3 | 20 | 6 | 3 | 3 |
| 2 | Candelilla wax | 3 | 20 | 6 | 3 | 3 |
| 3 | Microcrystalline wax | 6 | — | 6 | — | 6 |
| 4 | Polyethylene wax | 6 | — | 6 | — | 6 |
| 5 | Dextrin palmitate | — | — | — | 20 | — |
| 6 | Diglyceryl triisostearate | 10 | 10 | 10 | 10 | 10 |
| 7 | Propylene glycol dicaprate | 44.3 | 32.3 | 18.3 | 10.3 | 4.3 |
| 8 | Heavy liquid isoparaffin | 10 | 5 | 20 | 20 | 20 |
| 9 | Liquid lanolin acetate | 10 | 5 | 20 | 20 | 20 |
| 10 | Ester compound of Prep. Ex. 2 | — | — | — | — | — |
| 11 | Polycondensate of Prep. Ex. 1 | — | — | — | — | — |
| 12 | Tetra-ester compound of Comp. Prep. Ex. 1 | — | — | — | — | 20 |
| 13 | Dimethyldichlorosilane-treated fumed silica [1] | — | — | — | 3 | — |
| 14 | Silica beads [2] | — | — | — | 3 | — |
| 15 | Fluorinated red oxide-coated mica [3] | 2 | 2 | 2 | 2 | 2 |
| 16 | Silicone-treated titanated mica [4] | 2 | 2 | 2 | 2 | 2 |
| 17 | Red No. 202 | 0.1 | 0.1 | 0.1 | 0.1 | 0.1 |
| 18 | Yellow No. 4 | 0.6 | 0.6 | 0.6 | 0.6 | 0.6 |
| 19 | Titanium oxide | 1.5 | 1.5 | 1.5 | 1.5 | 1.5 |
| 20 | Black iron oxide | 0.1 | 0.1 | 0.1 | 0.1 | 0.1 |
| 21 | 2-ethylhexyl p-methoxycinnamate | 1 | 1 | 1 | 1 | 1 |
| 22 | Propyl p-hydroxybenzoate | 0.1 | 0.1 | 0.1 | 0.1 | 0.1 |
| 23 | 2,6-di-tert-butyl-p-cresol | 0.1 | 0.1 | 0.1 | 0.1 | 0.1 |
| 24 | dl-alpha-tocopherol | 0.1 | 0.1 | 0.1 | 0.1 | 0.1 |
| 25 | Perfume | 0.1 | 0.1 | 0.1 | 0.1 | 0.1 |
| Total | | 100 | 100 | 100 | 100 | 100 |

Evaluation items & results

| | | | | | | |
|---|---|---|---|---|---|---|
| (1) | Ease of use | Δ | X | X | X | Δ |
| (2) | Luster | Δ | X | Δ | X | X |
| (3) | Moisturizing feel | X | X | Δ | X | X |
| (4) | Shape retention properties | X | ○ | Δ | Δ | ○ |

Notes
[1] "Aerosil R-976S" made by Nippon Aerosil Co., Ltd.
[2] "Godd Ball D11-796C" made by Suzuki Yushi Industrial Co., Ltd.
[3] treated with perfluoroalkylphosphate ester diethanolamine salt (5% by mass)
[4] treated with dimethylpolysiloxane (3% by mass)

(Manufacturing Process)

Step A: After the ingredients 1 through 12 were heated to 110 to 120° C. and solved, the ingredients 13 through 20 were added and uniformly mixed.

Step B: The ingredients 21 through 24 were added to the mixture obtained in the step A, and uniformly mixed.

Step C: The ingredient 25 was added to the mixture obtained in the step B, and the resultant mixture was heated and subjected to air removing. Then, the mixture was charged into a mold and cooled to obtain a molded product.

(Evaluation)

1. Sensory Evaluation

To evaluate (1) the feeling realized by the use (ease of spreading), (2) the luster of coverage, and (3) the moisturizing feel, a sensory evaluation test was conducted using twenty special panel members. Each panel member assessed each sample product on the following absolute scale (a 0-to-6 scale). The scores given by all the panel members on each sample product were summated and the average score was calculated, from which the product was rated on four levels according to the evaluation criteria shown below.

(Absolute Scale)

<Score>: <Evaluation>
- 6: Excellent
- 5: Good
- 4: Fair
- 3: Ordinary
- 2: Slightly poor
- 1: Poor
- 0: Very poor (Rating on Four Levels)

| <Average score>: | <Rating> | |
|---|---|---|
| More than 5: | Excellent: | ◎ |
| More than 3 and 5 or less: | Good: | ○ |
| More than 1 and 3 or less: | Slightly poor: | Δ |
| 1 or less: | Poor: | X |

2. Shape retention properties

The lipstick was caused to protrude from the case and horizontally placed in a thermostat of 50° C. for one week. One week later, the state of the lipstick was observed and assessed on four levels (A to D) according to the state of the lipstick, from "no change" to "broken".

| <State>: | <Assessment> |
|---|---|
| No change: | ◎ |
| Slightly curved, but ignorable: | ○ |
| Curved: | Δ |
| Considerably curved or broken: | X |

As is apparent from Table 1 the lipsticks of the present invention not only showed excellent shape retention properties, but also spread smoothly when applied to the lips and provided a coverage with satisfactory luster and moisturizing feel. In contrast to this, the product of Comparative Example 1 not using the essential component (c) of the present invention was unfavorable especially in that the moisturizing feel and the shape retention properties were unsatisfactory. Although the shape retention properties were slightly improved in the product of Comparative Example 2, other properties were not satisfactory. The product of Comparative Example 3 where the heavy liquid isoparaffin was used instead of the essential component (c) according to the present invention was unsatisfactory especially in terms of the feeling realized by the use. The product of Comparative Example 4 where the heavy liquid isoparaffin was used instead of the essential component (c) according to the present invention and the combination of the dextrin fatty acid ester and silica was used as the oily gelling agent was unsatisfactory especially in terms of the feeling realized by the use, luster of the coverage and moisturizing feel. The product of Comparative Example 5 where the tetra-ester compound prepared in Comparative Preparation Example 1 was used instead of the essential component (c) according to the present invention was unsatisfactory especially in terms of luster of the coverage and the moisturizing feel.

EXAMPLE 8

Paste Type Lip Rouge

| (Ingredients) | (% by mass) |
|---|---|
| 1. 12-hydroxystearic acid | 1 |
| 2. Dextrin fatty acid ester | 3 |
| 3. Fumed silica coated with dimethyl-dichlorosilane [1] | 1 |
| 4. Aluminum isostearate | 1 |
| 5. Ester compound of Preparation Example 2 | 10 |
| 6. Heavy liquid isoparaffin | 25 |
| 7. Propylene glycol dicaprate | 10 |
| 8. Diglyceryl tetraisostearate | 20 |
| 9. UV absorber (Oxybenzone) | 0.1 |
| 10. Antioxidant (Vitamin E) | 0.1 |
| 11. Diisostearyl malate | 23.8 |
| 12. Pigment | 5 |
| Total | 100 |

Note
[1] "Aerosil R-976S" made by Nippon Aerosil Co., Ltd.

(Manufacturing Process)

Step A: After the ingredients 1 through 11 were uniformly mixed and solved under application of heat, the ingredient 12 was added and uniformly mixed.

Step B: The mixture obtained in the step A was charged into a mold to obtain a product.

The paste type lip rouge obtained in Example 8 smoothly spread, provided a coverage with satisfactory luster and moisturizing feel, and showed excellent shape retention properties without the presence of waste fluid.

On the other hand, when a product was manufactured using the tetra-ester compound obtained in Comparative Preparation Example 1 instead of the ester compound of Preparation Example 2 (the ingredient No. 5), the resultant product was inferior in terms of luster of the coverage and the moisturizing feel.

EXAMPLE 9

Paste Type Eye Gloss

| (Ingredients) | (% by mass) |
|---|---|
| 1. Glyceryl (behenate/eicosanedioate) | 2 |
| 2. Sucrose fatty acid ester [5] | 3 |
| 3. Organic modified bentonite [6] | 2 |
| 4. Diisostearyl malate | 10 |
| 5. Polycondensate of Preparation Example 1 | 25 |
| 6. Polybutene | 10 |
| 7. Ester compound of Preparation Example 2 | 25 |
| 8. Liquid lanolin | 10 |
| 9. UV absorber (2-ethylhexyl p-methoxycinnamate) | 0.1 |
| 10. Antioxidant (2,6-di-tert-butyl-p-cresol) | 0.1 |
| 11. Glyceryl trioctanoate | 12.8 |
| Total | 100 |

Note
[5] "Sugar Wax S-10E" made by Dai-ichi Kogyo Seiyaku Co., Ltd.
[6] "Benton 27" made by NL Industry Inc.

(Manufacturing Process)
Step A: The ingredients 1 through 11 were uniformly mixed and solved under application of heat.
Step B: The mixture obtained in the step A was charged into a mold to obtain a product.

The eye gloss obtained in Example 9 smoothly spread, provided a coverage with satisfactory luster and moisturizing feel, and showed excellent shape retention properties without the presence of waste fluid and phase separation.

EXAMPLE 10

Lip Cream

| (Ingredients) | (% by mass) |
|---|---|
| 1. Candelilla wax | 5 |
| 2. Ozokerite wax | 5 |
| 3. Fischer-Tropsch wax | 3 |
| 4. Bees wax | 3 |
| 5. Carnauba wax | 3 |
| 6. Polycondensate of Preparation Example 1 | 70 |
| 7. Vaseline | 10 |
| 8. UV absorber (Shea butter) | 0.1 |
| 9. Antioxidant (Vitamin E) | 0.1 |
| 10. Cetyl isooctanoate | 0.8 |
| Total | 100 |

(Manufacturing Process)
Step A: The ingredients 1 through 10 were uniformly mixed and solved under application of heat.
Step B: The mixture obtained in the step A was charged into a mold to obtain a product.

The lip cream obtained in Example 10 smoothly spread, offered sufficient moisturizing feel, and showed excellent shape retention properties.

According to the present invention, the oil-based cosmetic preparation according to the present invention can ensure excellent feeling realized by the use, i.e., ease of spreading, provided a coverage with excellent luster and moisturizing feel, and showed satisfactory shape retention properties.

What is claimed is:
1. An oil-based cosmetic preparation comprising:
   (a) an oily gelling agent;
   (b) an oil-based ingredient; and
   (c) at least one selected from the group consisting of
   an ester compound represented by the following formula (I) which is a reaction product of ditrimethylolpropane with 2-ethylhexanoic acid,
   polycondensates of ditrimethylolpropane with a dibasic carboxylic acid having 2 to 10 carbon atoms,
   polycondensates of the ester compound of the following formula (I) with a dibasic carboxylic acid having 2 to 10 carbon atoms,
   polycondensates of a branched saturated fatty acid having 8 to 18 carbon atoms with the polycondensate of the ditrimethylolpropane with the dibasic carboxylic acid having 2 to 10 carbon atoms, and
   polycondensates of ditrimethylolpropane, a branched saturated fatty acid having 8 to 18 carbon atoms and a dibasic carboxylic acid having 2 to 10 carbon atoms,

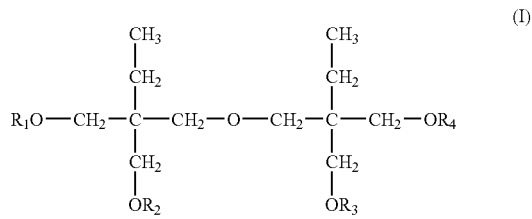

(I)

wherein $R_1$ to $R_4$ are each independently a hydrogen atom or 2-ethylhexanoic acid residue, provided that at least one of $R_1$ to $R_4$ represents 2-ethylhexanoic acid residue, wherein the component (c) has a hydroxyl value (OHV) of from 40 to 100.

2. The oil-based cosmetic preparation of claim 1, wherein the component (a) is at least one oily gelling agent selected from the group consisting of paraffin wax, ceresin wax, microcrystalline wax, Fischer-Tropsch wax, polyethylene wax, carnauba wax, and candelilla wax.

3. The oil-based cosmetic preparation of claim 1, wherein the component (a) is at least one oily gelling agent selected from the group consisting of 12-hydroxystearic acid, dextrin fatty acid esters, sucrose fatty acid esters, metallic soaps, silica, glyceryl (behenate/eicosanedioate), and organic modified clay minerals.

4. The oil-based cosmetic preparation of claim 1, wherein the component (b) is at least one oil-based ingredient selected from the group consisting of hydrocarbons, fats and oils, waxes, hardened oils, ester oils, fatty acids, higher alcohols, silicone oils, fluorinated oils and lanolin, liquid lanolin, lanolin acetate, liquid lanolin acetate, isopropyl esters of lanolin fatty acid and lanolin alcohols.

5. The oil-based cosmetic preparation of claim 1, wherein the component (c) is obtained by subjecting one equivalent of the ditrimethylolpropane and 1.5 to 3.5 equivalents of 2-ethylhexanoic acid, a dibasic carboxylic acid having 2 to 10 carbon atoms, or a mixture of a branched saturated fatty acid having 8 to 18 carbon atoms and a dibasic carboxylic acid having 2 to 10 carbon atoms to a reaction of esterification and/or dehydration condensation.

6. The oil-based cosmetic preparation of claim 1, wherein the component (c) is the ester compound represented by formula (I).

7. The oil-based cosmetic preparation of claim 1, wherein the component (c) is the polycondensate of the ditrimethyloipropane, the branched saturated fatty acid having 8 to 18 carbon atoms and the dibasic carboxylic acid having 2 to 10 carbon atoms.

8. The oil-based cosmetic preparation of claim 1, wherein the component (c) is a mixture of the ester compound represented by formula (I) and the polycondensate of the ditrimethylolpropane, the branched saturated fatty acid having 8 to 18 carbon atoms and the dibasic carboxylic acid having 2 to 10 carbon atoms.

9. The oil-based cosmetic preparation of claim 1, wherein the component (a) is contained in an amount of 0.5 to 30% by mass, the component (b) is contained in an amount of 1 to 95% by mass, and the component (c) is contained in an amount of 1 to 90% by mass.

10. The oil-based cosmetic preparation of claim 9, wherein the component (a) is contained in an amount of 1 to 20% by mass, the component (b) is contained in an amount of 3 to 70% by mass, and the component (c) is contained in an amount of 5 to 70% by mass.

* * * * *